United States Patent [19]

Sommer

[11] Patent Number: 5,750,411
[45] Date of Patent: May 12, 1998

[54] SOL PARTICLE DECAY PROTECTION IMMUNOASSAY

[75] Inventor: Ronald G. Sommer, Elkhart, Ind.

[73] Assignee: Bayer Corporation, Elkhart, Ind.

[21] Appl. No.: 656,904

[22] Filed: Jun. 3, 1996

[51] Int. Cl.$^6$ .................... G01N 33/543; G01N 33/544; G01N 33/553
[52] U.S. Cl. .................... 436/525; 436/501; 436/517; 436/518; 436/528; 436/529; 436/531; 436/535; 435/4; 435/71
[58] Field of Search .................... 435/4, 7.1; 436/501, 436/517, 525, 518, 528, 529, 531, 535

[56] References Cited

U.S. PATENT DOCUMENTS

| | | | |
|---|---|---|---|
| 4,313,734 | 2/1982 | Leuvering | 23/230 |
| 4,853,335 | 8/1989 | Olsen et al. | 436/527 |

OTHER PUBLICATIONS

Roth et al, J. Histochem & Cytochem, 1978; 26:163–9.
Leuvering et al, Journal of Immunochemical Methods, 60 (1983), pp. 9–23.
Leuvering et al: J. Immunol. Meth., 1981, vol. 45, pp. 183–194.

*Primary Examiner*—Ponnathapura Achutamurthy
*Attorney, Agent, or Firm*—Jerome L. Jeffers

[57] ABSTRACT

Disclosed is a method for determining the concentration of an analyte in a liquid test sample. The method involves the use of colloidal sized metal particles, which exhibit a spectral response in the agglomerated state which is detectably different than in their unagglomerated state, which bear specific binding partners for the analyte in question on their surface. The specific binding partner treated colloidal particles are combined in a buffered, aqueous medium with a destabilizer material capable of destabilizing the specific binding partner-colloidal particle conjugates thereby permitting the particles to agglomerate. Also included in the liquid medium is a polymer bearing multiple analyte or analyte analog molecules along its surface which serves to protect the specific binding partner coated metal particles from dissociation by the destabilizing agent. Analyte added to the medium, typically in the form of a fluid test sample, competes for the specific binding partner and thereby decreases the amount of protection afforded by the analyte or analyte analog bearing polymer which permits unprotected colloidal particles to agglomerate and provide a detectable spectral response. The magnitude of the change in spectral response is directly proportional to the concentration of analyte in the fluid test sample.

25 Claims, 6 Drawing Sheets

SOL PARTICLE DECAY PROTECTION IMMUNOASSAY

BACKGROUND OF THE INVENTION

Homogeneous immunoassays using antibodies conjugated to colloidal gold sol particles have been described. Thus, Leuvering et al discuss the detection of human chorionic gonadotrophin (hCG) using gold sol particles coated with antibodies to hCG in *Journal of Immunochemical Methods*, 60 (1983) Pp. 9–23. This article discusses the detection of hCG using a classical agglutination method in which antibodies specific to 2 or more of the analyte's antigenic sites are used, so that a cross-linked matrix will form in the presence of analyte. This reference discloses carrying out the agglutination reaction in a buffered medium containing NaCl and polyethylene glycol to enhance the agglutination and reports greater background in the presence of PEG. This sort of assay requires that agglutination take place and results in a disappearance of color or, in the case of agglutination inhibition, the inhibition of color loss. In U.S. Pat. No. 4,313,734 there is described the use of metal sols as antibody labels and it is pointed out that metal sol particles carry a charge which confers a stabilizing effect due to mutual repulsion and that flocculation occurs in the presence of strong electrolytes. It is also pointed out that flocculation can be prevented by coating the particles with macromolecules possessing polar groups such as proteins, polyethylene glycols, polymeric carbohydrates or polyvinyl alcohols.

In gold sol agglutination inhibition assays, there is used an agglutinator with multiple copies of analyte bound to a polymer to bind the antibody-gold sol conjugate. This binding causes agglutination resulting in loss of color. Thus, the presence of analyte which are usually low molecular weight moieties, inhibits agglutination by binding to the antibody-gold sol conjugate thereby decreasing the loss of color.

Roth et al describe a shift in color from red to blue when gold sol which is unprotected by protein flocculates in solution: *J. Histochem & Cytochem* 1978; 26:163–9. They describe the preparation of lectin-gold complexes which are stabilized. Those samples which had insufficient lectin protection experienced a color change of the gold sol from red to blue when the NaCl was added.

The present invention involves a sol particle immunoassay method in which agglutination does not take place and which results in a color change rather than the disappearance of color.

SUMMARY OF THE INVENTION

The present invention involves a method for determining the concentration of an analyte in a fluid test sample. The method comprises the steps of:

a) combining the fluid test sample containing the analyte with a buffered aqueous system suitable for the binding of the analyte with a specific binding partner therefor. The aqueous system contains colloidal sized metal particles having a specific binding partner for the analyte or analyte analog bound to their surface and a polymer having analyte moieties or analogs thereof that will bind to the specific binding partner covalently attached along the polymer chain. This results in the formation of an association between the polymer and the metal particles via the specific binding partner for the analyte which association serves to protect the metal particles;

b) adding a destabilizer material to the aqueous system which is capable of causing aggregation of the colloidal metal particles with the specific binding partner bound to their surface if the specific binding partner is not bound to the analyte or analyte analog moieties attached to the polymer chain;

c) measuring the spectral properties of the colloidal sized particles at a wavelength at which the aggregated colloidal particles are known to absorb; and d) comparing the measured spectral properties with the same spectral properties obtained using fluid samples having known concentrations of analyte to thereby determine the concentration of analyte in the fluid test sample.

DESCRIPTION OF THE INVENTION

Figure 1:
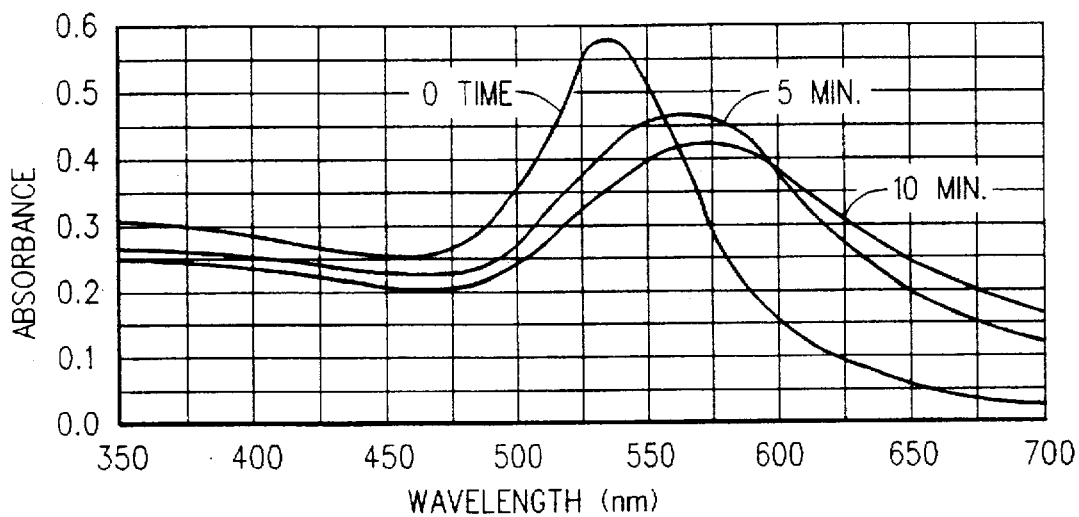
FIG. 1 illustrates the spectral shift, from lower to higher wavelengths achieved using the method of the present invention.

The following discussion of the present invention involves the use of gold sol as the colloidal labeling particle. However, other metal sols can be used as direct particulate labels such as silver sols and those in which palladium or selenium comprise the label material. Typically, the metal particles are at least 5 to 500 nm in diameter with a particle size of 10 to 100 nm being preferred. Also suitable are colloidal sized particles of metal compounds or polymer nuclei coated with a metal or metal compound.

The invention is predicated on the fact that colloidal sized metal particles tend to absorb light at one wavelength when they are in the dispersed state and at a different wavelength when the particles aggregate, i.e. they change color. Colloidal particles tend to aggregate in liquid media due to charge-charge and/or hydrophobic interactions. However, these particles are resistant to aggregation when proteins are bound to their surfaces. These proteins can be in the form of specific binding partners, e.g. antibodies; wherein the analyte being sought is the antigen, lectins and carbohydrates, hormones and hormone receptors, enzymes and enzyme substrates, biotin and avidin, vitamins and vitamin binding proteins, complimentary polynucleotide sequences, drugs and receptors, enzymes and inhibitors, aproteins and co-factors and growth factors and receptors. This resistance to aggregation is believed to result from adsorption of the protein on the surface of the metal sol which shields the sol particles from the attractive forces which cause them to aggregate. However, certain substances such as high salt concentrations or high concentrations of PEG can cause the colloidal metal particles with the specific binding partner adsorbed thereto to aggregate and display a color change. In the presence of the polymer-analyte conjugate, the specific binding of the antibody with analyte molecules (or analogs thereof) which are attached to the polymer-analyte conjugate stabilize the metal sol particles to which the specific binding partner is adsorbed against aggregation. This binding, at multiple sites by analyte molecules on the same polymer molecule, may make it more difficult for antibody molecules to dissociate from the surface of the metal sol particles or may provide a protective layer which inhibits aggregation. In either case, analyte which is present in the test fluid will compete with the analyte (or analogs) attached to the polymer for binding sites of the specific binding partner. This reduces the degree of protection afforded by the polymer in direct relationship to the concentration of analyte present in the test fluid. The unprotected metal sol particles can aggregate due to charge/charge or hydrophobic forces in the presence of a destabilizer and this aggregation can be detected by measuring the spectral properties of the aqueous system. Spectral properties that change with the aggregation of the colloidal particles include shifting of the spectral peak to higher wavelengths and the resultant change in absorption at other wavelengths. Light scattering techniques may also be used. The spectral property most commonly measured is absorbance as determined by the shift in peak spectral wavelength and the resultant change in absorbance at other wavelengths. The destabilizer materials are believed to cause dissociation of the particle and proteinaceous binding partner by disrupting the hydrophobic or charge-charge interactions which keep the specific binding partner absorbed to the metal particle surface. Suitable destabilizing materials include polyethylene glycols; inorganic salts such as sodium chloride, potassium chloride, ammonium sulfate or sodium sulfate; salts of ionizible organic molecules such as citric acid, tartaric acid, acetic acid or tris (hydroxymethyl) amino methane and polymers other than polyethylene glycol having similar polarity thereto such as, for example, polyvinylpyrolidone, polyvinyl alcohol, polymethyl vinyl ether or water soluble polycarbonates. Polyethylene glycol is a preferred destabilizing agent with PEG having a molecular weight of from 1,000 to 20,000 at a concentration of 2% to 10% (w/v) in the aqueous system being especially advantageous. The concentration of salt, when used as the destabilizing agent, will vary depending on the particular salt and the forces holding the specific binding partner to the metal sol particle. In general, a concentration of 100 mM to 1,500 mM (preferably 500 mM to 1,000 mM) is suitable for the desired purpose.

The particle-binding partner conjugate can be protected from the effects of the destabilizer material, e.g. PEG, by including in the aqueous system a polymer having covalently bound thereto multiple copies of the analyte or an analog thereof. The analyte would be the strongest binding molecule for the specific binding partner which is absorbed to the metal sol. An analog of the analyte, i.e. a chemically modified molecule related to the analyte which has measurable binding affinity for the specific binding partner, could be attached to the polymer in lieu of the analyte.

Suitable polymers for this element of the present invention include Ficoll®, a nonionic synthetic polymer of sucrose, polyaspartic acid, Gantrez AN [poly (methylvinylether/maleic anhydride)] and polylysine. Any water soluble polymer that can be derivatized so that the analyte or analog thereof can be attached to multiple sites along its chain, can be used. Thus, in the presence of a sufficient amount of polymer having multiple analyte or analyte analog molecules bound to it, the metal particle-binding partner complex will specifically bind to the analyte or analog molecules carried by the polymer and be protected from the effects of the destabilizing material so that no aggregation of the particles and hence no change in spectral properties will occur.

However, in the presence of analyte from the fluid test sample, the protective effect of the analyte-polymer conjugate is inhibited by the occupation of some of the specific binding sites on the metal particles by analyte from the sample. This type of competitive assay differs from the classical agglutination reaction which is also known to take place at certain concentrations, usually higher than needed for the present assay, of these same conjugates, in that in the present system the analyte-polymer conjugate protects against aggregation of the antibody-metal sol conjugate (and the resultant shift in spectral color) while in classical agglutination, the analyte-polymer conjugate causes aggregation which results in a shift in spectral color or a loss of color. In the present invention, the amount of signal, such as an increase in absorbance at a wavelength at which the aggregated particles are known to absorb, is directly related to the weakening of the protection offered by the polymer-analyte conjugate and this weakening of protection is directly proportional to th e concentration of analyte in the fluid test sample. In the case of the particulate label being a gold sol, the spectral response is a shift from magenta, the color of the protected/unaggregated gold sol, to a purple/blue color which is the color of the deprotected gold sol after it has formed aggregates. The magenta to purple/blue shift increases in the presence of increasing amounts of analyte and its intensity can be followed either visually or with a spectrophotometer.

The aqueous system in which the present analysis is carried out is typically buffered to a pH of from 5 to 9 depending on the pH at which the analyte binds best to the antibody/metal sol conjugate. This is mediated by the pH dependence of the antibody binding to the analyte. The system can be used for the determination of virtually any analyte against which antibodies can be produced and which can be attached to the backbone of a polymer such as Ficoll®. Such analytes, in addition to the pyridinoline and deoxypyridinoline employed in the following example, include therapeutic drugs such as theophyline and digoxin and proteins such as human serum albumin and hemoglobin $A_1C$. The fluid test sample analyzed with the use of this invention is typically urine, although other body fluids such as blood serum, blood plasma, spinal fluid and sweat can be analyzed for the presence of analyte.

EXAMPLE

A gold sol conjugate of 50 nm gold sol and monoclonal antibody against pyridinoline (PYD) was prepared as follows:

1. A 5 mL of 50 nm gold sol, PN/EMGC50, Goldmark Biologicals; Phillipsburg, N.J. was placed in a glass beaker and the pH adjusted to 7.4 with 0.2M phosphoric acid.
2. With rapid stirring 27.3 µL of a solution containing 41 micrograms of 6H2 monoclonal anti-PYD antibody from Metra Biosystems, Mountain View, Calif. was added and mixed for two minutes.
3. 250 µL of 1% PEG 20,000 was added to the 5 mL aliquot of gold sol while stirring rapidly.
4. 500 µL of 10% bovine serum albumin (BSA) was added while stirring rapidly.
5. the resulting gold sol/antibody conjugate was isolated by a 10 minute centrifugation at 12,000×g.
6. Approximately 90% of the supernatant was removed and the gold sol conjugate was resuspended in 5 mL of 1% BSA with 0.05% PEG 20,000 pH 7.4.
7. After the wash procedure was repeated 4 times (5$^{th}$ centrifugation) the gold sol conjugate was resuspended with the same wash buffer as in step 6 to a volume of 750 µL (per 5 mL gold sol used in step 1) and kept refrigerated in a glass vial.

Figure 2:
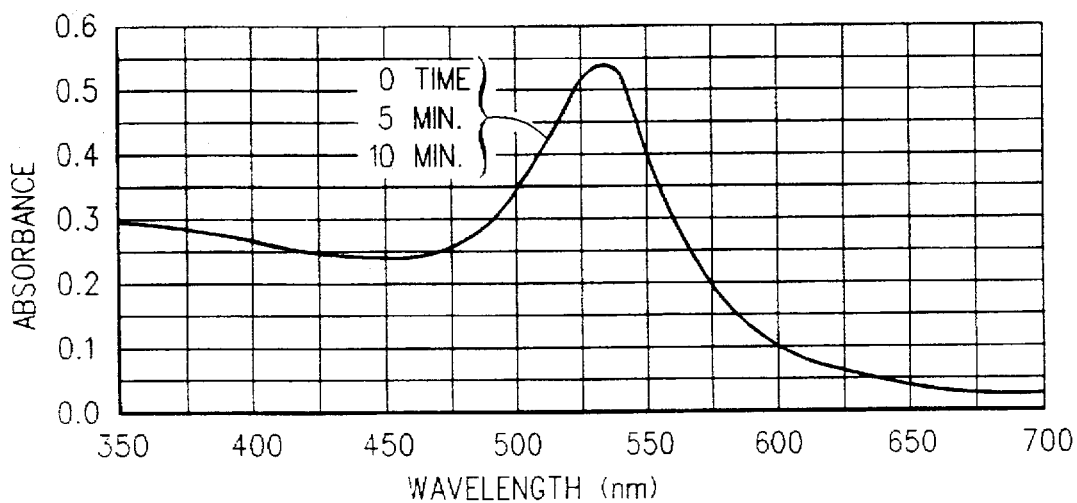
FIG. 2 illustrates the absence of a spectral shift when the gold sol is protected with PEG 20,000.

The conjugate, 50 µL, was added to 750 µL of a buffered solution consisting of 50 mM TRIS Cl and 3 mM magnesium acetate as buffer together with 4% (w/v) PEG 8000. The buffer maintained the solution at pH 7.8. It was observed that the gold sol conjugate was unstable as indicated by a spectral shift with time as determined by measuring the spectra between 350 nm and 700 nm using an HP 8452A uV/VIS spectrophotometer at 0, 5 and 10 minutes after addition of the antibody-gold sol conjugate. This spectral shift, from lower to higher wavelengths, i.e. red to blue, is illustrated by FIG. 1. It is believed that the shift from red to blue results from aggregation of the gold sol which occurs when it is placed in certain solutions in the free (unprotected) form as reported by J. Roth et al in *J. Histochem & Cytochem* 1978; 26:163–169). This instability was not found when the control gold sol, prepared in the same manner as the antibody/gold sol conjugate but without antibody, was added to the buffered solution. The absence of a spectral shift is illustrated by FIG. 2 which indicates that the BSA and PEG 20,000 that are absorbed to the entire surface of the control gold sol is a better protective agent than the antibody.

Figure 3:
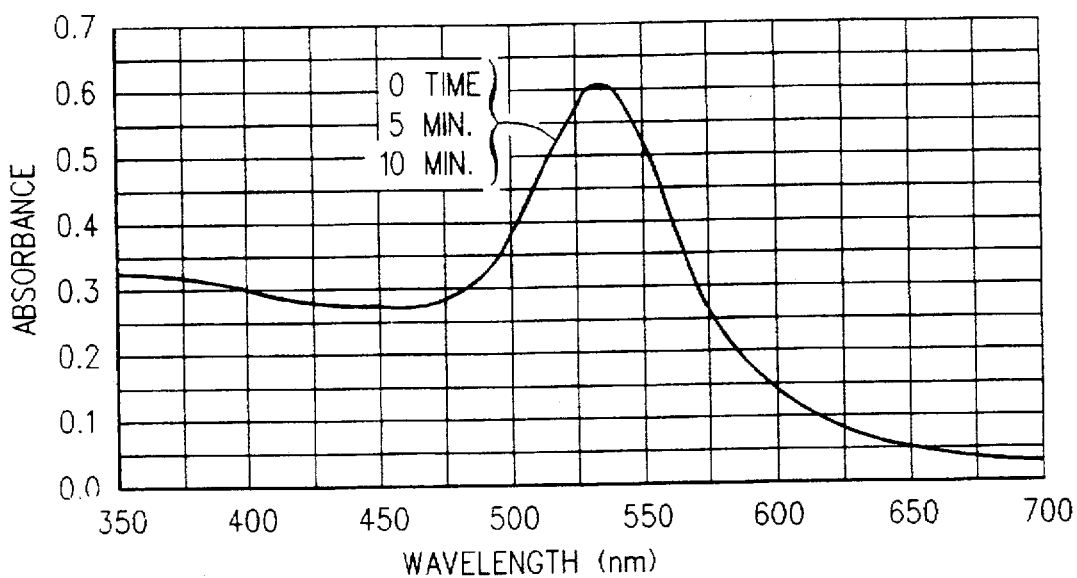
FIG. 3 illustrates the protection from destabilization that is afforded to the antibody gold sol conjugate by PYD-Ficoll®.

In a separate experiment, 1.56 nM PYD-Ficoll® polymer (molecular weight 400,000 daltons with 19 PYD moieties per molecule) was added to the buffer, followed by the gold sol/antibody conjugate. The gold sol was completely stable as indicated by the spectra of FIG. 3 indicating that the binding of the PYD-Ficoll® to the antibody gold sol conjugate protected the conjugate from the destabilization that occurred in the experiment illustrated by FIG. 1.

Figure 4:
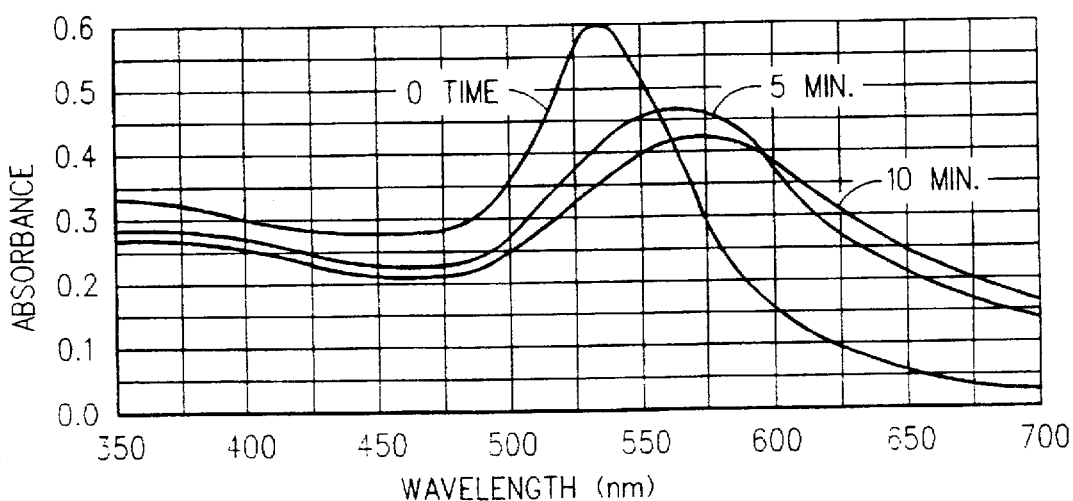
FIG. 4 demonstrates that the change in the gold sol spectra takes place even in the presence of control Ficoll®.

To verify that the effect noted above was not caused by the Ficoll itself without a contribution from the PYD moieties, 1.56 nM control Ficoll (no PYD attached) was added to the buffer before adding the antibody/gold sol conjugate. The spectra of FIG. 4 demonstrate that the change in the gold sol spectra takes place even in the presence of the control Ficoll®.

Figure 5:
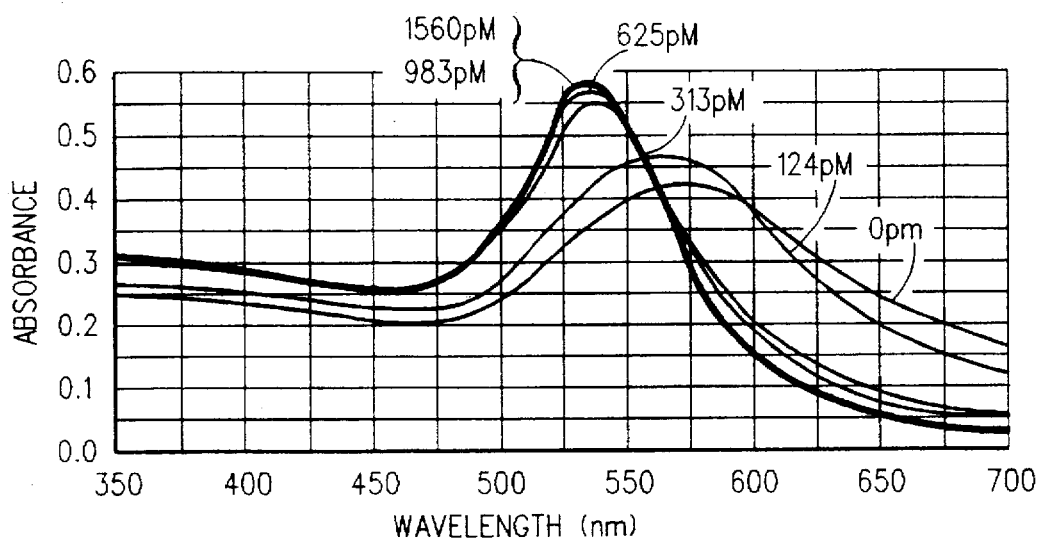
FIG. 5 shows the spectra 10 minutes after gold sol conjugate addition for various amounts of PYD-Ficoll® in buffer.

Next, the amount of PYD-Ficoll® necessary to provide protection to the gold sol conjugate was investigated. FIG. 5 shows the spectra 10 minutes after the gold sol conjugate addition for various amounts of PYD-Ficoll® in the buffer and indicates that the protection is complete at some concentration below 1000 pM PYD-Ficoll®.

Figure 6:
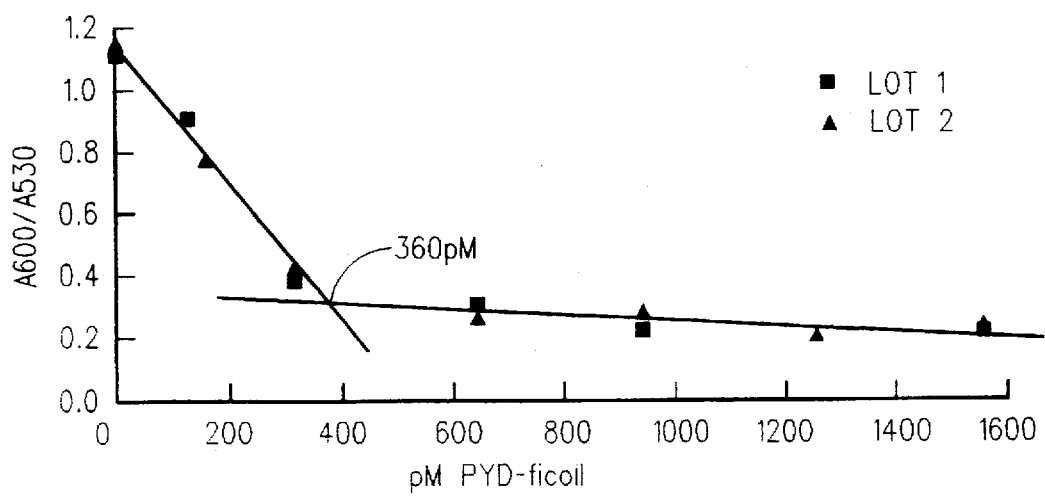
FIG. 6 graphically represents data from 10 minute spectra as the ratio of absorbance at 600 nm to the absorbance at 530 nm-vs-PYD-Ficoll® concentration.

FIG. 6 graphically presents data from the 10 minute spectra for lots 1 and 2 of the gold-antibody conjugate plotted as the ratio of absorbance at 600 nm to the absorbance at 530 nm-vs-PYD-Ficoll® concentration. FIG. 6 illustrates a typical binding curve in which the amount of PYD-Ficoll® necessary to stabilize the amount of gold sol conjugate is 360 pM as determined by the intersection of the lines. The amount of gold sol conjugate was kept constant in each assay at approximately $1.5 \times 10^{10}$ particles per assay and the amount of PYD-Ficoll® was the same for both lots.

Figure 7:
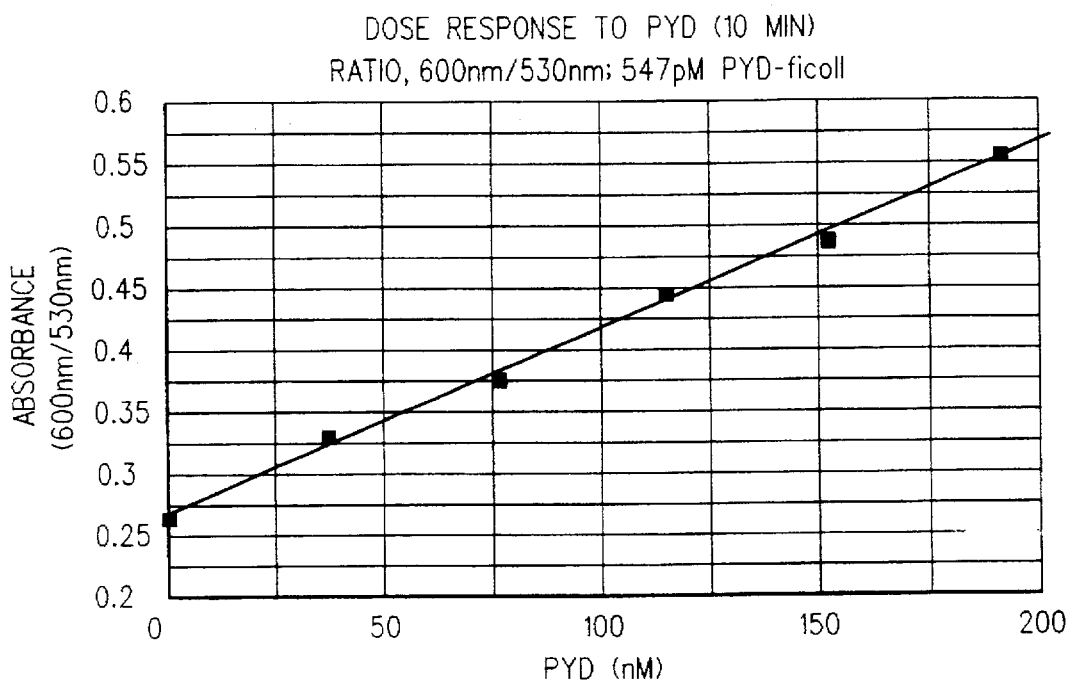
FIG. 7 shows the PYD dose response obtained when various concentrations of PYD were added to 750 µL of buffer containing 547 nm PYD-Ficoll®.

Since the protective effect of the PYD-Ficoll® was a result of the specific binding of the PYD on the PYD-Ficoll® to the antibodies thereto on the particle, it was postulated that the binding could be inhibited by PYD and that the extent of this inhibition should be proportionate to PYD concentration. This was found to be true. FIG. 7 shows the PYD dose response obtained when various concentrations of PYD were added to 750 µL of the buffer containing 547 nM PYD-Ficoll® before the addition of 50 µL of the gold sol.

Figure 8:
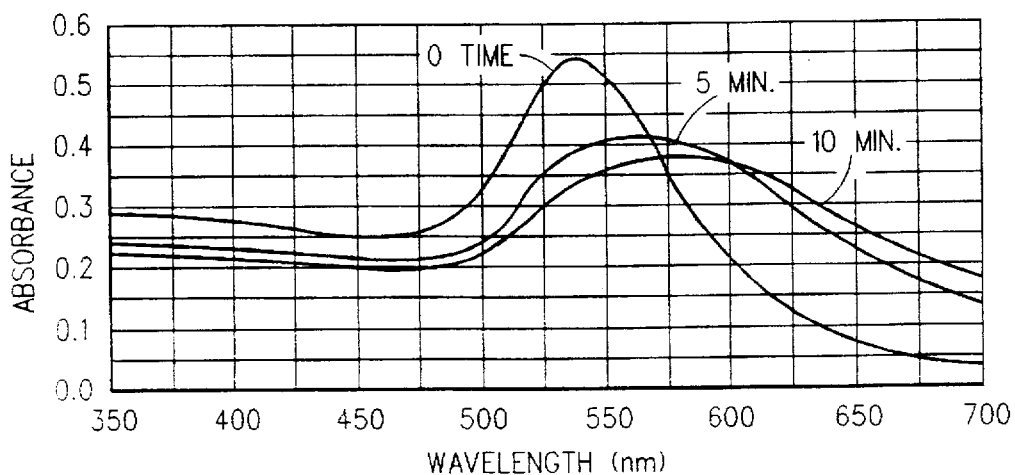
FIG. 8 graphically illustrates the results obtained using a gold sol conjugate of a monoclonal antibody against deoxypyridinoline (DPD).
Figure 9:
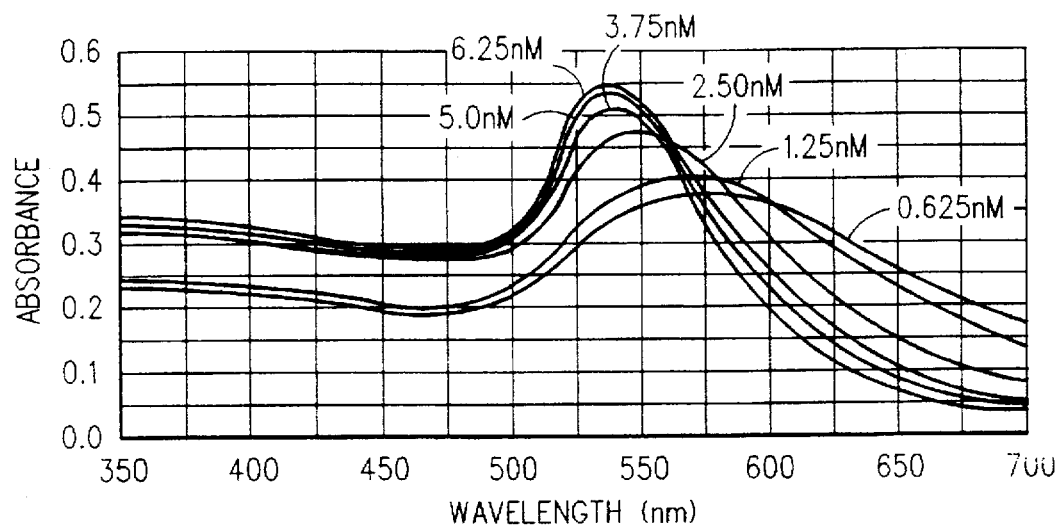
FIG. 9 shows the 10 minute spectra obtained using DPD-Ficoll® having a linker arm inserted between the Ficoll and the DPD.
Figure 10:
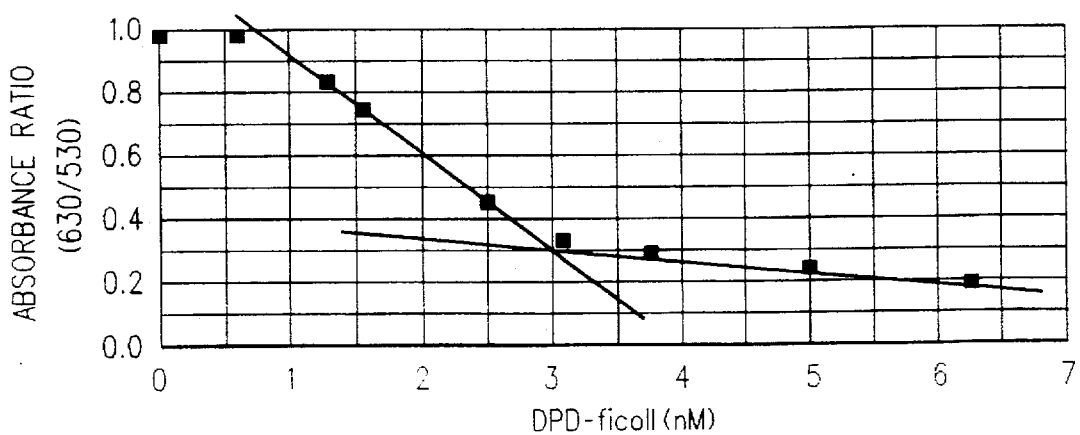
FIG. 10 illustrates the binding curve which was obtained by plotting the ratio of the absorbencies at 630 nm to the absorbencies at 530 nm for a 10 minute spectra.

In another experiment, it was found that similar results could be obtained using a 60 nm gold sol conjugate of a monoclonal antibody against deoxypyridinoline (DPD). In FIG. 8 there is shown the instability of this conjugate in the previously described buffer. A DPD-Ficoll® conjugate was prepared using Ficoll® having a molecular weight of 400,000 daltons with each molecule containing approximately 13 DPD moieties. In this conjugate, a linker arm of approximately 8 carbon atoms was inserted between the Ficoll® and the DPD. FIG. 9 shows the 10 minute spectra of this gold conjugate in the presence of various concentrations of DPD-Ficoll® and FIG. 10 illustrates the binding curve which was obtained by plotting the ratio of the absorbencies at 630 nm to the absorbencies at 530 nm for the 10 minute spectra.

Figure 11:
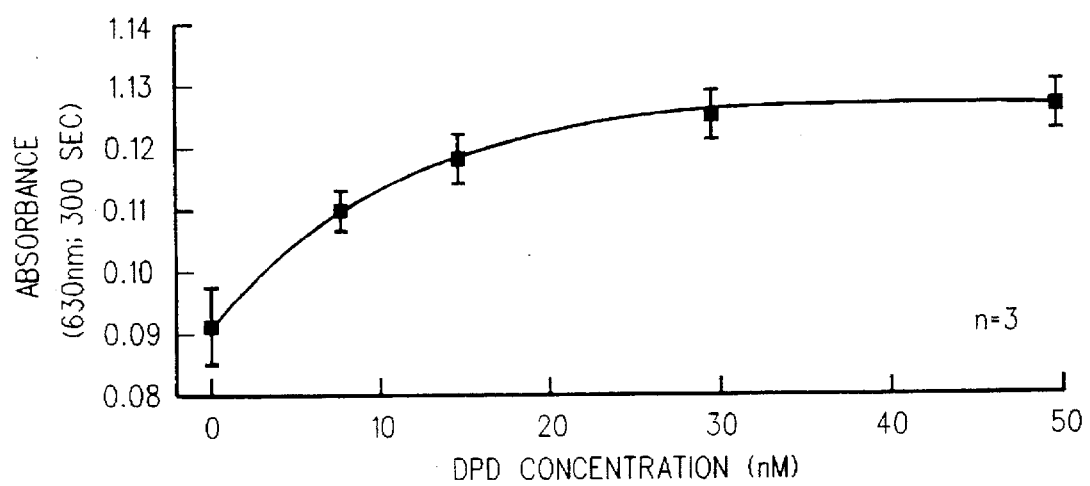
FIG. 11 was obtained by inhibiting the protective effect of the DPD-Ficoll® on the gold sol-anti DPD conjugate thereby allowing it to agglomerate and absorb light at 630 nm.

Using the ratio of gold sol anti-DPD conjugate to DPD-Ficoll just above the 3 nM DPD-Ficoll® equivalence point, i.e. 3.5 nM, a dose response to DPD was developed on the Cobas Fara Centrifugal Analyzer manufactured by Hoffmann-LaRoche. This dose response which is shown in FIG. 11 was obtained by inhibiting the protective effect of the DPD-Ficoll® on the gold sol-anti DPD conjugate thereby allowing it to agglomerate and absorb light at 630 nm. The protective effect was inhibited by the DPD in the sample.

What is claimed is:

1. A method for determining the concentration of an analyte in a fluid test sample which method comprises the steps of:

a) combining the fluid test sample containing the analyte in a buffered aqueous system suitable for the binding of the analyte with a specific binding partner thereto, which aqueous system contains colloidal sized metal particles having a specific binding partner for the analyte or analyte analog bound to their surface and a polymer bearing a plurality of analyte moieties or analogs thereof covalently attached along the polymer chain which will bind to the specific binding partner bound to the metal particles to thereby form an association between the polymer and the metal particles in which the metal particles are protected by the polymer;

b) adding a destabilizer material to the aqueous system which is capable of causing aggregation of the colloidal metal particles with the specific binding partner bound to their surface to destabilize the colloidal metal particles which are not protected by the polymer from the specific binding partner attached thereto to cause the metal particles which are not associated with the polymer to aggregate;

c) measuring the spectral properties exhibited by the colloidal metal particles at a wavelength at which the aggregated colloidal particles are known to absorb; and d) comparing the spectral properties with spectral properties obtained using fluid samples having known concentrations of analyte to thereby determine the concentration of analyte in the fluid test sample.

2. The method of claim 1 wherein the metal particles are gold, silver, palladium or selenium.

3. The method of claim 2 wherein the metal is gold.

4. The method of claim 1 wherein the metal particles are from 5 to 500 nm in diameter.

5. The method of claim 4 wherein the metal particles are from 10 to 100 nm in diameter.

6. The method of claim 1 wherein the polymer is a nonionic synthetic polymer of sucrose, polyaspartic acid, poly(methylvinyl ether/maleic anhydride), or polylysine.

7. The method of claim 1 wherein the destabilizer material is a polyethylene glycol, an inorganic salt, or a salt of an ionizable organic molecule.

8. The method of claim 7 wherein the destabilizer material is an inorganic salt.

9. The method of claim 7 wherein the destabilizer material is polyethylene glycol in a concentration of from 2 to 10% (w/w).

10. The method of claim 8 wherein the destabilizer material is sodium chloride, potassium chloride, ammonium sulfate or sodium sulfate.

11. The method of claim 9 wherein the inorganic salt is present in a concentration of from 100 nM to 1,500 nM.

12. The method of claim 7 wherein the destabilizer material is citric acid, tartaric acid, acetic acid or tris (hydroxymethyl) amino methane.

13. The method of claim 10 wherein the concentration is from 500 nM to 1,000 nM.

14. The method of claim 1 wherein the destabilizer material is a polymer having a polarity similar to that of polyethylene glycol.

15. The method of claim 14 wherein the polymer is polyvinylpyrolidone, polyvinyl alcohol, polymethyl vinyl ether or a water soluble polycarbonate.

16. The method of claim 1 wherein the analyte is deoxypyridinoline and the fluid of the fluid test sample is urine.

17. The method of claim 1 wherein the spectral property measured is the intensity of light absorbed by the metal particles measured at a wavelength at which agglomerates of the metal particles are known to absorb.

18. The method of claim 1 wherein the comparison is made by comparing the intensity of the absorbed light from the fluid test sample with a curve of intensity of absorbed light-vs-analyte concentration which curve has been prepared by treating fluid samples containing known concentrations of analyte in the manner of steps a–c and plotting analyte concentration against intensity of absorbed light.

19. The method of claim 1 wherein the specific binding partner is an antibody against the analyte.

20. A method for determining the concentration of an analyte in a urine test sample which method comprises the steps of:

a) combining the urine test sample containing the analyte with a buffered aqueous system suitable for the binding of the analyte with an antibody thereto, which aqueous system contains colloidal sized gold particles having an antibody specific to the analyte bound to their surface and a polymer bearing a plurality of analyte moieties covalently attached along the polymer chain which will bind to the antibody bound to the gold particles to thereby form an association between the polymer and the gold particles in which the gold particles are bound by the polymer;

b) adding polyethylene glycol to the aqueous system to destabilize the colloidal gold particles which are not protected by the polymer from the antibody attached thereto to cause the gold particles which are not associated with the polymer to aggregate;

c) measuring the intensity of light absorbed by the gold particles at a wavelength at which aggregates of the gold particles are known to absorb; and d) comparing the intensity of the absorbed light with that obtained using fluid samples having known concentrations of analyte to thereby determine the concentration of analyte in the fluid test sample.

21. The method of claim 20 wherein the polyethylene glycol has a molecular weight of from about 1,000 to about 20,000 and is present in the aqueous system at a concentration of from about 3% to about 10% (w/v).

22. The method of claim 20 wherein the polymer is a nonionic synthetic polymer of sucrose.

23. The method of claim 20 wherein the analyte is deoxypyridinoline.

24. The method of claim 19 wherein the antibody is a monoclonal antibody.

25. The method of claim 20 wherein the antibody is a monoclonal antibody.

* * * * *